United States Patent
Kaluski

(10) Patent No.: US 8,043,320 B2
(45) Date of Patent: Oct. 25, 2011

(54) BIFURCATED BALLOON & STENT DELIVERY SYSTEM

(76) Inventor: Edo Kaluski, Florham Park, NJ (US)

( * ) Notice: Subject to any disclaimer, the term of this patent is extended or adjusted under 35 U.S.C. 154(b) by 0 days.

(21) Appl. No.: 12/515,741

(22) PCT Filed: Feb. 26, 2008

(86) PCT No.: PCT/IL2008/000242
§ 371 (c)(1),
(2), (4) Date: May 21, 2009

(87) PCT Pub. No.: WO2008/152620
PCT Pub. Date: Dec. 18, 2008

(65) Prior Publication Data
US 2010/0094247 A1    Apr. 15, 2010

Related U.S. Application Data

(60) Provisional application No. 60/929,099, filed on Jun. 13, 2007.

(51) Int. Cl.
*A61M 29/00* (2006.01)
(52) U.S. Cl. .................................... 606/194; 604/96.01
(58) Field of Classification Search .................. 604/284, 604/96.01, 103.05; 606/108, 191, 194–195, 606/198; 623/1.11–1.12, 1.35, 901
See application file for complete search history.

(56) References Cited

U.S. PATENT DOCUMENTS

| | | | | |
|---|---|---|---|---|
| 4,994,071 A | * | 2/1991 | MacGregor | 606/194 |
| 6,013,054 A | * | 1/2000 | Jiun Yan | 604/103.07 |
| 6,017,324 A | | 1/2000 | Tu et al. | |
| 6,099,497 A | * | 8/2000 | Adams et al. | 604/96.01 |
| 2002/0120327 A1 | | 8/2002 | Cox et al. | |
| 2003/0093109 A1 | | 5/2003 | Mauch | |
| 2006/0293695 A1 | | 12/2006 | Ricci et al. | |
| 2007/0100301 A1 | | 5/2007 | Gumm | |

FOREIGN PATENT DOCUMENTS

WO    WO 2008/152620    12/2008

OTHER PUBLICATIONS

International Search Report Dated Jan. 9, 2009 From the International Searching Authority Re.: Application No. PCT/IL2008/000242.
Written Opinion Dated Jan. 9, 2009 From the International Searching Authority Re.: Application No. PCT/IL2008/000242.
International Preliminary Report on Patentability Dated Jan. 28, 2010 From the International Bureau of WIPO Re.: Application No. PCT/IL2008/000242.
Supplementary European Search Report and the European Search Opinion Dated Mar. 14, 2011 From the European Patent Office Re. Application No. 08710242.2.
Communication Pursuant to Rules 70(2) and 70a(2) EPC Dated Mar. 31, 2011 From the European Patent Office Re. Application No. 08710242.2.

* cited by examiner

*Primary Examiner* — S. Thomas Hughes
*Assistant Examiner* — Ashley Cronin

(57) ABSTRACT

A bifurcated balloon for in vivo use, comprises: a proximal hollow tubular element, two bifurcating hollow tubular elements extending distally from a distal end of the proximal hollow tubular element, each of the two elements comprising: a first distal tubular element guidable into a first branch of a vessel bifurcation, and a second distal tubular element guidable into a second branch of the vessel bifurcation. The bifurcated balloon further comprises a longitudinal chamber extending from a distal end of the first distal tubular element, and a first substantially longitudinal guidewire channel passing through the longitudinal chamber, the first guidewire channel having two ends of which a first end passes through a proximal portion of the longitudinal chamber.

7 Claims, 6 Drawing Sheets

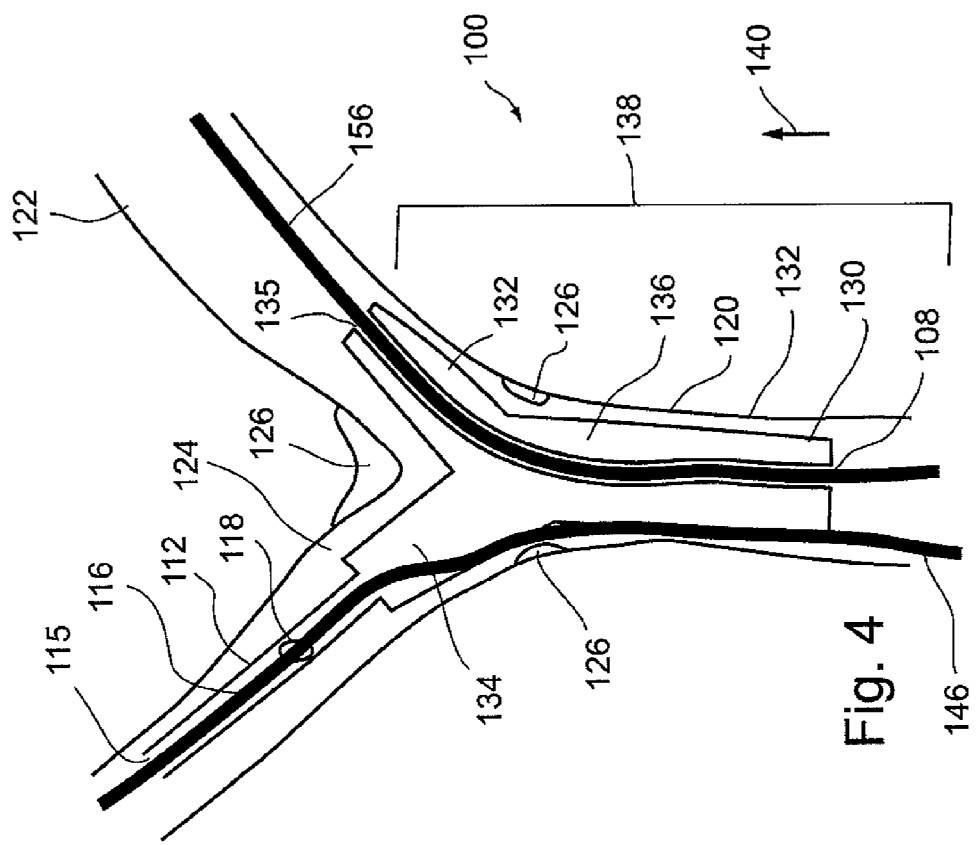
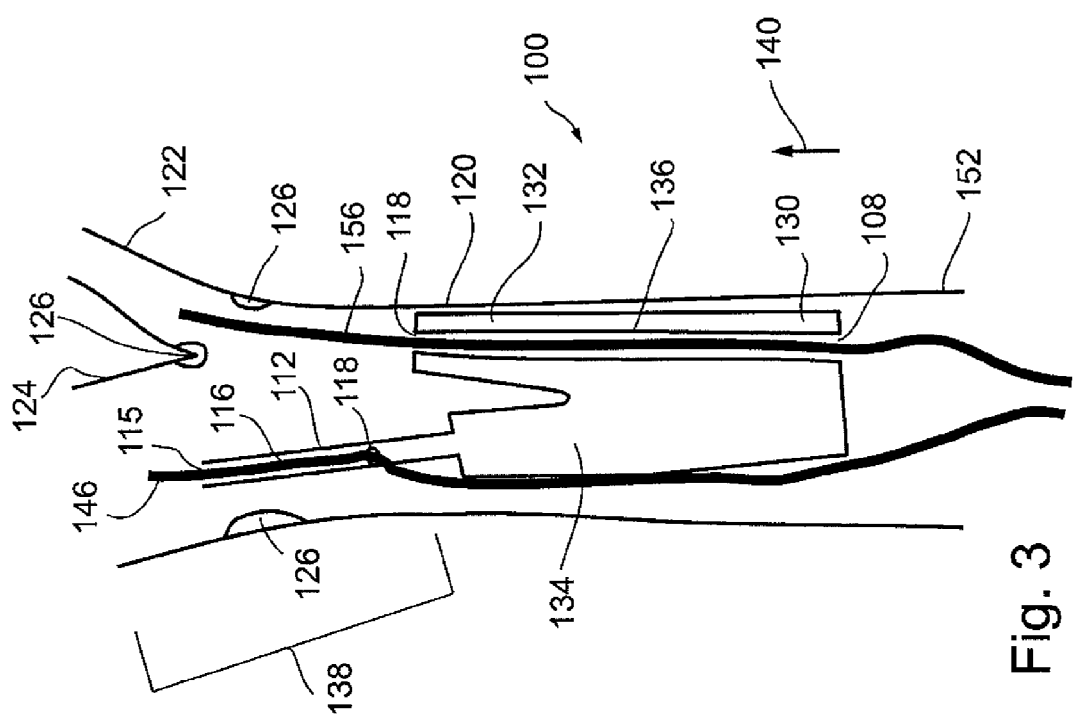

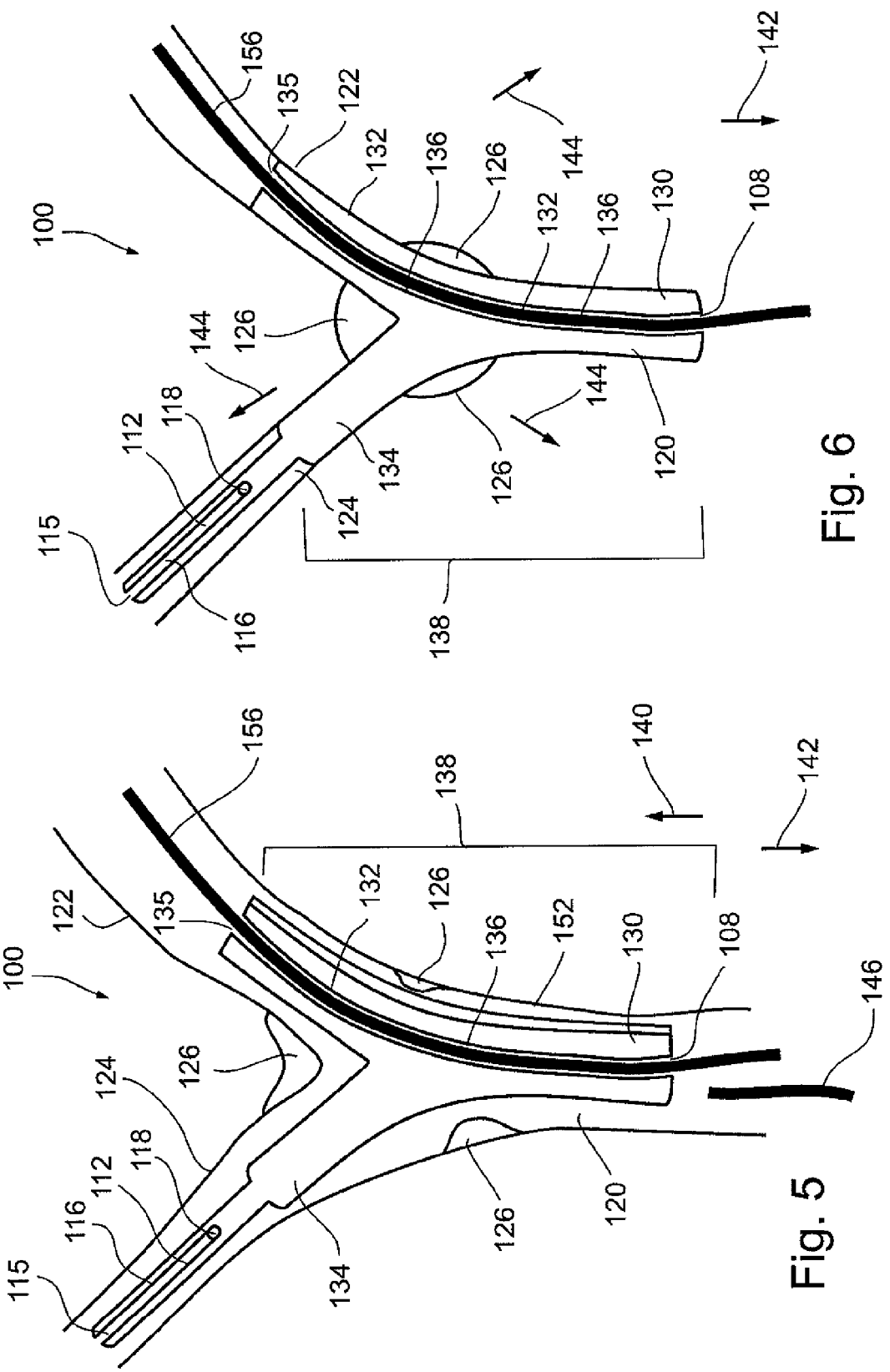

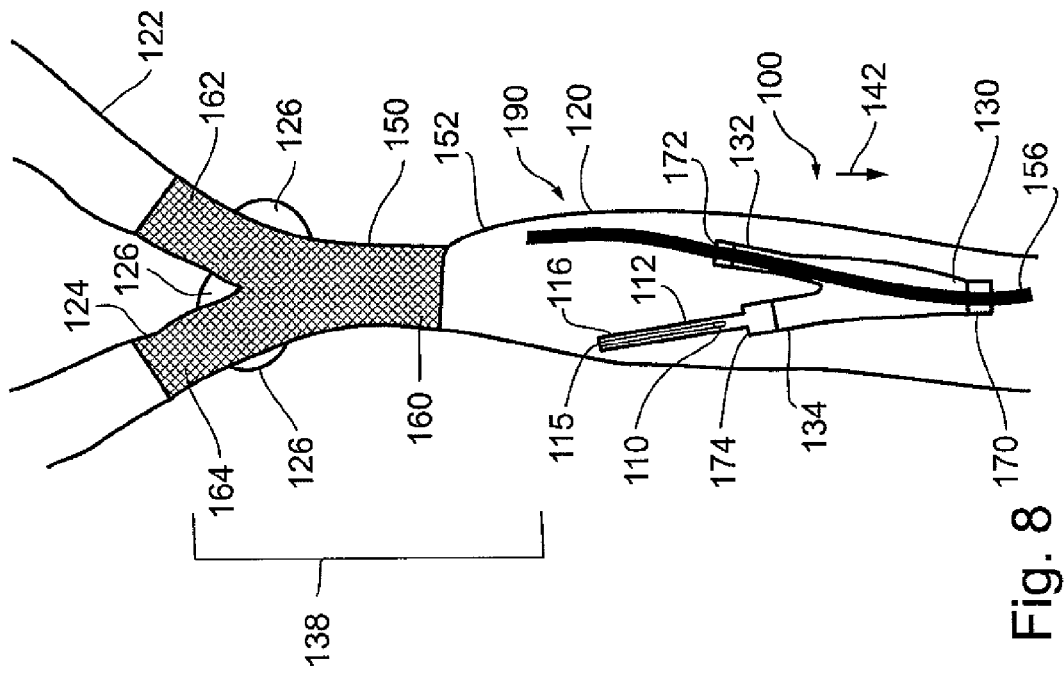
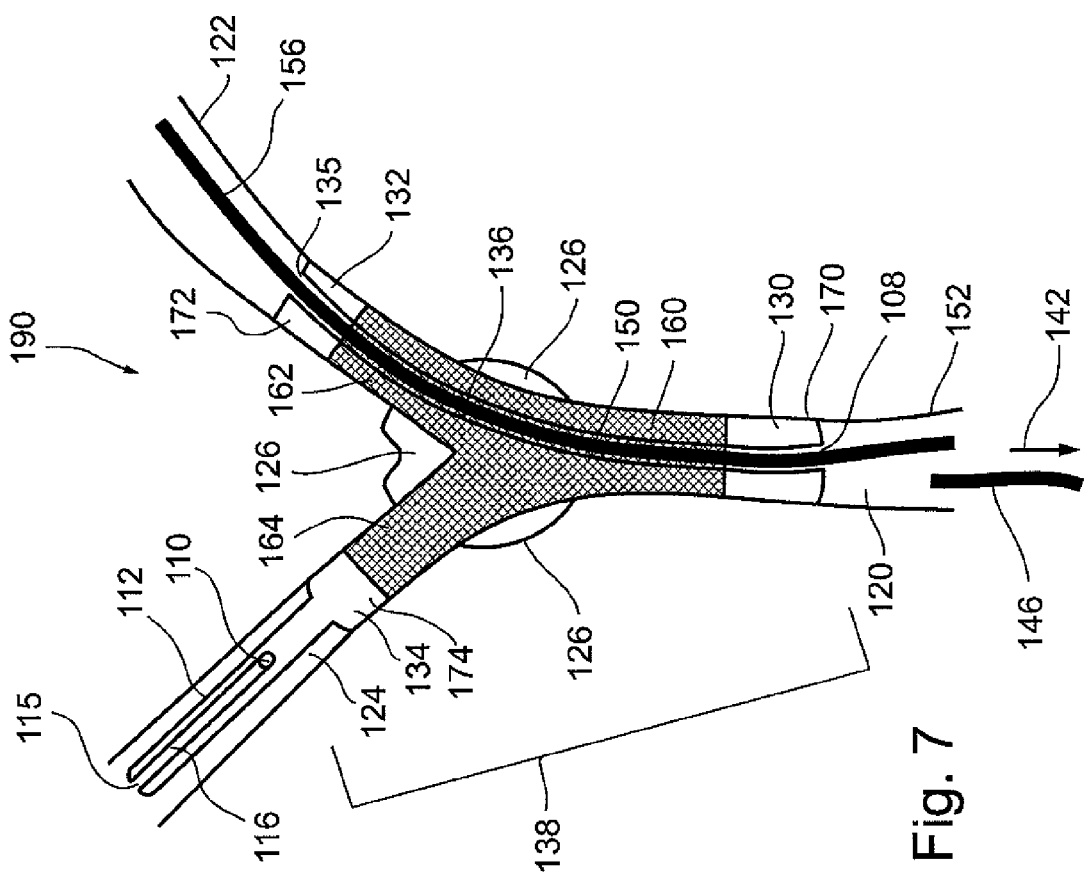

BIFURCATED BALLOON & STENT DELIVERY SYSTEM

RELATED APPLICATIONS

This Application is a National Phase of PCT Patent Application No. PCT/IL2008/000242 having International filing date of Feb. 26, 2008, which claims the benefit of U.S. Provisional Patent Application No. 60/929,099 filed on Jun. 13, 2007. The contents of the above Applications are all incorporated herein by reference.

FIELD AND BACKGROUND OF THE INVENTION

The present invention relates to endovascular balloons used to recanalize, dilate and/or deploy a stent within a constricted vessel.

Balloon angioplasty for opening a constricted segment of a blood vessel has become a widely accepted therapeutic alternative to coronary and peripheral arterial bypass surgery for many patients.

To deliver a balloon catheter used in balloon angioplasty, a guidewire is advanced through the vasculature across the constricted vessel segment. A dedicated guidewire lumen in the balloon portion of the catheter is fed over the guidewire; the dedicated lumen substantially spanning the longitudinal length of the balloon interior. The balloon is advanced along the guidewire through the vasculature until reaching the constricted vessel segment. The balloon is inflated to apply radial outward pressure against the walls of the constricted vessel segment to restore vessel patency, and normal vessel diameter.

When used to deploy a stent in the constricted vessel segment, the unexpanded stent is mounted around the unexpanded balloon and transported to the constricted vessel segment. Upon reaching the constricted vessel segment, the balloon and stent are expanded, thereby restoring patency and normal vessel diameter to the constricted vessel and providing a structure that will continue to support the vessel wall.

The precise positioning of the balloon against the constricted vessel segment is critical to the success of the procedure; yet, many factors can adversely affect balloon deliverability and precise positioning.

The human vascular tree is far from being uniform in structure and each procedure is a unique experience requiring considerable manual dexterity. With currently available balloon systems, certain lesions are inaccessible and/or exceedingly difficult to reach due to vessel narrowing and rigidity of the treated vessel and lesions. Hence, the unexpanded balloon should be designed with a narrow cross sectional diameter (crossing profile).

Vascular balloon dilation is more challenging when the constricted vessel segment is located within a bifurcation in the vessel: where a sizable side branch vessel bifurcates off a main branch vessel. A common treatment technique consists of inflating two balloons sequentially; a first balloon in the main branch vessel followed by a second balloon in the side branch vessel.

Unfortunately, sequential dilatations are frequently ineffective in treating bifurcated constricted vessels, as the vessel wall at the bifurcation tends to stretch outward; resulting in narrowing of the adjacent branch or shifting atherosclerotic debris from one vessel to the other, referred to as "shifting plaque".

In order to prevent adjacent branch narrowing, a "kissing balloon" technique has been developed, as described in U.S. Pat. No. 4,896,670 (Crittenden), the entirety of which is incorporated herein by reference. In the kissing balloon technique, a first balloon occupies the proximal main branch vessel (trunk) and a segment of the distal main branch vessel. A second balloon occupies a segment of the proximal main branch (trunk) and a segment of the side branch vessel. Prior to inflation, the proximal portions of the two balloons occupy the proximal main branch vessel sit side-by-side and, upon inflation, the first proximal balloon portion "kisses" the second proximal balloon portion.

The "kissing balloon" technique is not without drawbacks, including:

a) difficulty of coordinating inflation and deflation of two separate balloons using two separate inflators by two operators;

b) creation of asymmetric and non-circular expansion of the proximal main branch (MB) where the "kissing" takes place, potentially causing suboptimal post-inflation results. For example, underexpansion will fail to properly clear the stenotic segments; while overexpansion can cause a dissection (tear) of the vessel wall.

c) balloon slippage during inflation;

d) difficulty in positioning the side-by-side balloon segments due to the large crossing profile created by the separate guidewires and guidewire lumens in each balloon; and e) difficulty in manipulating the guiding catheters as the catheters must accommodate two separate side-by-side balloons of at least 6 French (2.0 millimeters) or 7 French (2.3 millimeters).

U.S. Pat. No. 4,413,989 (Schjeldahl et al) and U.S. Pat. No. 6,017,324 (Tu, et al), the entirety of which are incorporated herein by reference, disclose a "Y"-shaped balloon, herein bifurcated balloon.

As seen in FIG. 1a, a prior art bifurcated balloon 180 has two guidewire lumens:

a first guidewire lumen 136 passing through a proximal balloon trunk 130 and a first distal balloon branch 132; and a second guidewire lumen 107 passing through proximal balloon trunk 130 and a second distal balloon branch 134.

The bifurcated balloon solves some of the problems posed by the kissing balloons. However, when guidewires 106 and 156 are fed through guidewire lumens 136 and 107 respectively, the large crossing profile hinders deliverability and accurate positioning of bifurcated balloon 180.

Additionally, two separate side-by-side guidewire lumens 106 and 156 increase the complexity and cost of manufacturing bifurcate balloon 180.

It would be highly advantageous to have a bifurcated balloon that deploys in bifurcated vessels without having at least some of the disadvantages of the prior art.

SUMMARY OF THE INVENTION

The present invention successfully addresses at least some of the shortcomings of prior art by providing a bifurcated balloon wherein there is a maximum of one guidewire lumen passing through the bifurcated balloon; thereby substantially reducing balloon crossing profile, manufacturing complexity and production cost.

According to the teachings of the present invention there is provided a bifurcated balloon having a proximal trunk and two distal bifurcating balloon arms, comprising a first distal balloon portion; and a second distal balloon portion.

The bifurcated balloon includes a first guidewire lumen involving the proximal balloon trunk and a first distal balloon portion; and a second guidewire lumen that passes through a longitudinal extension tube which extends distally from a second distal balloon portion. First and second guidewires pass through the first and second guidewire lumens respectively.

In embodiments, the second guidewire lumen passes into the extension tube via an end-hole at the distal end of the extension tube, and out through a side-hole in the proximal portion of the extension tube.

When deployed with a stent having a single trunk and two distal bifurcating stent portions, the low bulk of the bifurcated balloon allows greater compaction of the stent in the unexpanded state, accruing precise balloon and stent placement and rapid deployment that ensures the patency of the bifurcated vessels.

According to the teachings of the present invention there is also provided a method of manufacturing a rapid exchange bifurcated balloon, comprising:

providing a bifurcating balloon having two distal balloon portions extending from a proximal balloon portion and a longitudinal distal tubular extension from a distal end of one of the two distal balloon portions. Additionally, the method includes making a side hole in a sidewall of the tubular extension, boring a distal hole in a distal end of the tubular extension; and connecting a guidewire lumen between the side hole and the distal hole.

In embodiments, the method further includes, extending a second longitudinal tubular extension from a distal end of a second of the two distal balloon portions. In such cases, the method includes making a side hole in a sidewall of the second tubular extension, boring a distal hole in a distal end of the second tubular extension; and connecting a guidewire lumen between the side hole and the distal hole of the second tubular extension.

According to one aspect of the present invention, there is provided a bifurcated balloon for in vivo use, comprising: a proximal hollow tubular element, two bifurcating hollow tubular elements extending distally from a distal end of the proximal hollow tubular element, each of the two elements comprising: a first distal tubular element guidable into a first branch of a vessel bifurcation, and a second distal tubular element guidable into a second branch of the vessel bifurcation. The bifurcated balloon further comprises a longitudinal chamber extending from a distal end of the first distal tubular element, and a first substantially longitudinal guidewire channel passing through the longitudinal chamber, the first guidewire channel having two ends of which a first end passes through a proximal portion of the longitudinal chamber.

In embodiments, the second end of the first substantially longitudinal guidewire channel passes through a distal end of the longitudinal chamber.

In embodiments, the second end of the first substantially longitudinal guidewire channel passes through a distal portion of the longitudinal chamber.

In embodiments, the apparatus includes a first guidewire insertable through the substantially longitudinal guidewire channel.

In embodiments, the apparatus includes a second substantially longitudinal guidewire channel passing through a proximal end of the proximal hollow tubular element and through a distal end of the second distal tubular element.

In embodiments, the apparatus includes a second guidewire insertable through the second substantially longitudinal guidewire channel.

In embodiments, the apparatus includes a second longitudinal chamber extending from a distal end of the second distal tubular element, and a second substantially longitudinal guidewire channel passing through the second longitudinal chamber, the second guidewire channel having two ends of which a first end passes through a proximal portion of the longitudinal chamber.

In embodiments, the second substantially longitudinal guidewire channel passes through a distal end of the longitudinal chamber.

In embodiments, the apparatus includes a second guidewire insertable through the second substantially longitudinal guidewire channel.

In embodiments, the apparatus includes a catheter channel from a proximal end of the proximal hollow tubular element.

According to another aspect of the invention, there is provided a method of manufacturing a rapid exchange bifurcated balloon, comprising: extending a longitudinal distal tubular extension from a distal end of a first of two distal balloon portions extending from a proximal portion of a bifurcated balloon, and creating a guidewire channel through the first longitudinal tubular extension.

In embodiments, the method includes extending a second longitudinal tubular extension from a distal end of a second of the two distal balloon portions, and creating a guidewire channel through the second longitudinal tubular extension.

According to still another aspect of the invention, there is provided a method of deploying a bifurcated balloon, comprising: providing a bifurcated balloon having a first guidewire channel through a proximal balloon portion and a first distal balloon portion and a second guidewire channel through a longitudinal tubular guidewire extension extending from a second distal balloon portion, passing a first guidewire through a proximal main branch vessel and a distal MB vessel and a second guidewire through the proximal MB vessel and a side branch vessel, feeding the first guidewire channel over the first guidewire, feeding the second guidewire channel over the second guidewire, moving the bifurcated balloon upward along the first and second guide wires, and visualizing the proximal and the first distal portion of the bifurcated balloon portion in the MB vessel and the second distal portion of the bifurcated balloon in the SB vessel.

According to still another aspect of the invention, there is provided a bifurcated self-expandable stent and using a method of advancing and positioning the bifurcated self-expandable stent involving using either one or two longitudinal tubular extension tubes which may be positioned distal to the stent and which accommodate the guide wire on which the self expandable stent is advanced.

In embodiments, the method includes inflating the bifurcated balloon, deflating the bifurcated balloon, and removing the bifurcated balloon from the SB vessel and the MB vessel.

The present embodiments successfully address the shortcomings of the presently known configurations by providing a bifurcated balloon wherein there is a maximum of a single guidewire lumen passing through the bifurcated balloon; thereby substantially reducing balloon crossing profile, manufacturing complexity and production cost.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques, and procedures for accomplishing a given task including, but not limited to, those manners, means, techniques, and procedures either known to, or readily developed from known manners, means, techniques, and procedures by practitioners of cardiology and cardiologic surgery.

BRIEF DESCRIPTION OF THE DRAWINGS

The invention of a bifurcated balloon having, at any given cross section throughout the length of the bifurcated balloon, a maximum of one guidewire lumen, is herein described, by way of example only, with reference to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a shows a known bifurcated balloon configuration;

FIG. 1b shows a bifurcated balloon in an expanded configuration, according to embodiments of the invention;

FIG. 2 shows guidewires in a cross-section of a bifurcated vessel, according to embodiments of the invention;

FIGS. 3-6 show deployment of the bifurcated balloon of FIG. 1b in a cross-section of a bifurcated vessel, according to embodiments of the invention;

FIG. 7 shows a bifurcated stent and bifurcated balloon assembly in an expanded configuration in a cross-section of a bifurcated vessel, according to embodiments of the invention;

FIG. 8 shows the bifurcated stent of FIG. 7 deployed in a cross-section of a bifurcated vessel, according to embodiments of the invention; and FIG. 9 shows an alternative embodiment of the bifurcated balloon shown in FIG. 1b, according to embodiments of the invention.

DESCRIPTION OF THE PREFERRED EMBODIMENTS

Figure 1A:
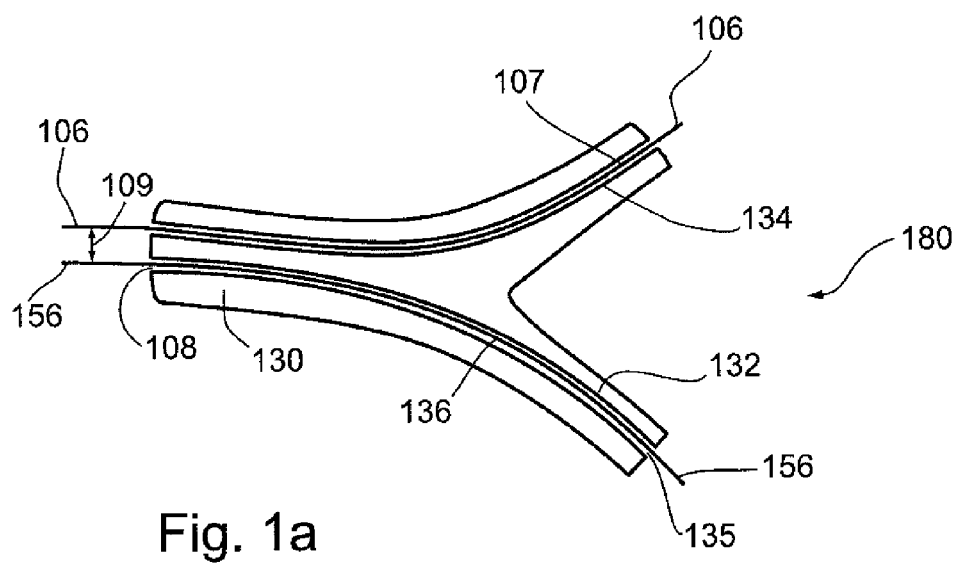

The present embodiments concern a bifurcated balloon having, at any given cross section throughout the length of the bifurcated balloon, a maximum of one guidewire lumen, thereby accruing a bifurcated balloon having a low bulk that is easily maneuvered through the vasculature.

The principles and operation according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways.

Also, it is to be understood that the phraseology and terminology employed herein is for the purpose of description and should not be regarded as limiting.

Generally, the nomenclature used herein and the laboratory procedures utilized in the present invention include techniques from the fields of medicine, biology, chemistry, material sciences and engineering. Such techniques are thoroughly explained in the literature.

Unless otherwise defined, all technical and scientific terms used herein have the same meaning as commonly understood by one of ordinary skill in the art to which the invention belongs. In addition, the descriptions, materials, methods, and examples are illustrative only and not intended to be limiting. Methods and materials similar or equivalent to those described herein can be used in the practice or testing of the present invention.

Figure 1B:
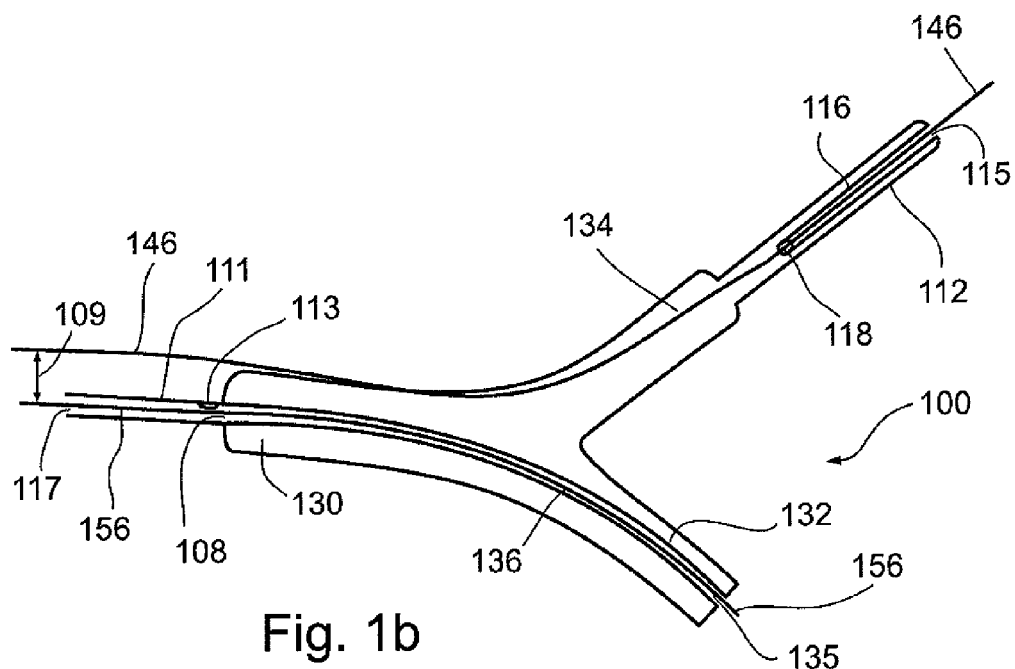

Referring now to the figures:

FIG. 1b shows an embodiment of a bifurcated balloon 100 in an expanded form having a trunk, herein proximal main branch (MB) balloon portion 130 and two distal balloon portions extending distally therefrom: distal MB balloon portion 132 and side branch (SB) balloon portion 134. As used herein with respect to balloon 100, the term "proximal" refers to a portion of balloon 100 that is nearer to the operator; the term "distal" refers to a portion of balloon 100 that is farther away from the operator.

Longitudinal MB guidewire lumen 136 extends from a proximal opening 108 catheter through proximal end of MB portion 130 and through a distal opening 135 through distal end of MB portion 132.

A guide wire 156 has been fed through guidewire lumen 136 into a catheter 111. In embodiments, guidewire 156 exits a proximal end opening 117, a configuration referred to as an "over the wire" system. In other embodiments, guide wire 156 exits out of a catheter side hole 113 proximal to bifurcated balloon 100, a configuration referred to as a "rapid exchange" system. The proximal opening can be an end-opening (117) or a side opening (113) or may open at any segment of the balloon catheter shaft proximal to the balloon itself.

Typically, catheter 111 connects to bifurcating balloon 100 with a halo tube (not shown) through which contrast material is introduced during inflation and withdrawn during deflation of bifurcated balloon 100.

In embodiments, an SB extension tube 112 extends distally from a distal end of SB balloon portion 134 and typically has a smaller diameter than SB balloon portion 134.

SB extension tube 112 includes an SB guidewire lumen 116 having a proximal side opening 118 passing through sidewall of SB extension tube 112 and a distal end opening 115 through the distal end of SB extension tube 112.

SB guidewire lumen 116 comprises a rapid exchange configuration that is significantly more distal and not traversing via the lumen of bifurcated balloon 100 as opposed to the case of lumen 107 of bifurcated balloon 180 (FIG. 1a); and allows rapid loading of balloon 100, via SB guidewire lumen 116 onto a guidewire 146 (FIG. 1b).

While opening 118 is shown approximately at about 1.5 centimeters distal to the distal end of SB balloon portion 134, opening 118 could be located further proximally, closer to the distal end of SB balloon portion 134 or further distally, closer to distal end opening 115.

Alternatively, distal end opening 115 could be positioned proximally on the side of SB extension tube 112, nearer to the distal end of SB balloon portion 134. The many options for configuring openings 115 and 118, providing easy mounting of SB guidewire housing on guidewire 146, are well known to those familiar with the art.

SB guidewire 146 passes externally to MB balloon portion 130 and SB balloon portion 134 so that only MB guidewire lumen 136 passes through bifurcated balloon 100; a configuration that greatly reduces the bulk of bifurcated balloon 100 both in the predeployed and expanded configurations as compared to bifurcated balloon 180 (FIG. 1A).

Additionally, the inclusion of one guidewire channel 136 through bifurcated balloon 100 (FIG. 1B) reduces the complexity of bifurcated balloon 100, and related manufacturing costs.

Furthermore, as SB guidewire 146 passes externally to MB balloon portion 130, distance 109 (FIG. 1B) between guidewires 156 and 146 is considerably greater than distance 109 (FIG. 1a) associated with bifurcated stent 180; a distance that aids in preventing entanglement of guidewires 146 and 156 while maneuvering bifurcated balloon 100 through the vasculature in a predeployed state.

Figure 2:
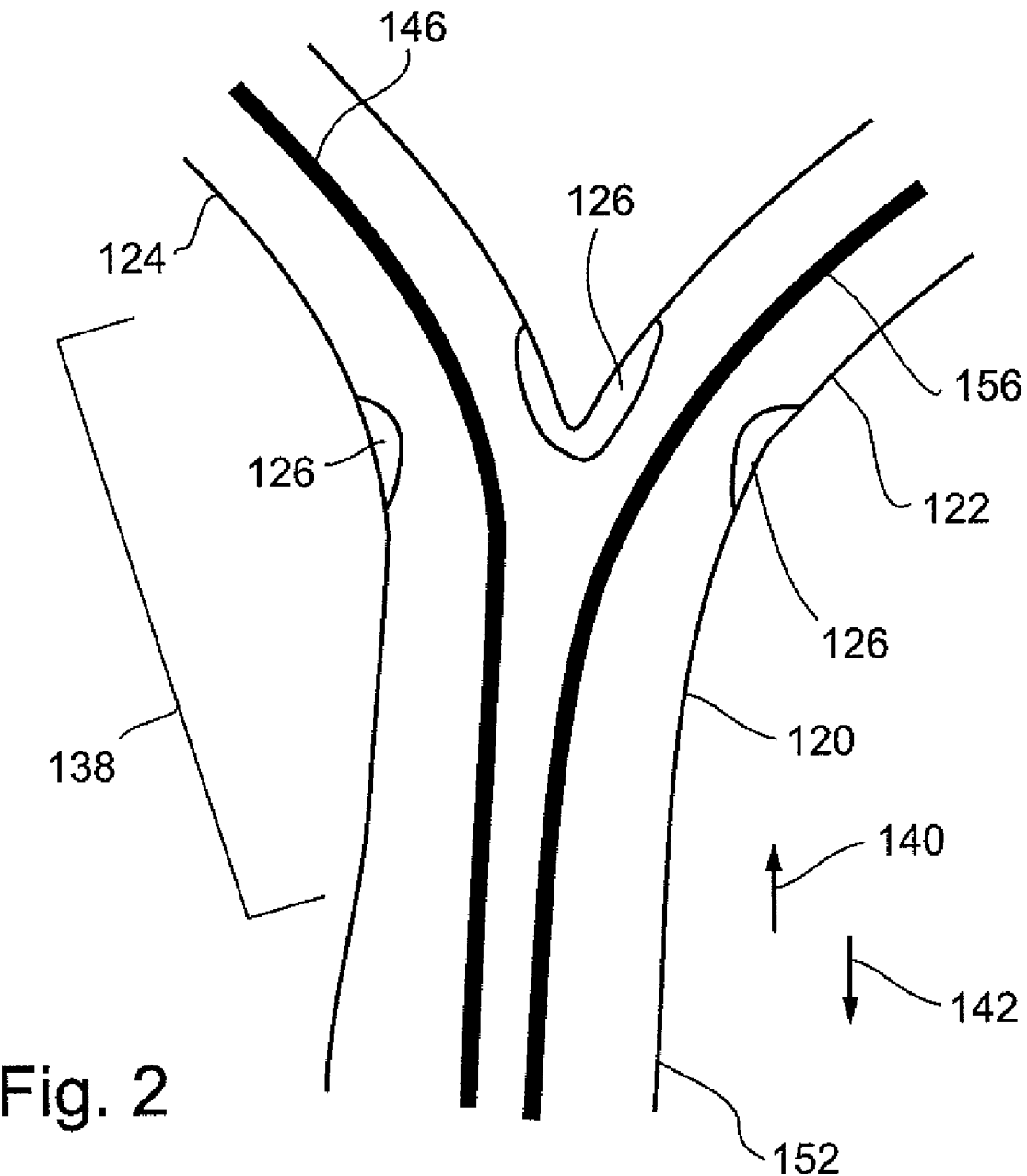

FIG. 2 shows a constricted, herein stenotic, vessel 152 with stenotic plaques 126 located along MB proximal vessel segment 120, MB distal vessel segment 122 and SB vessel segment 124.

As used herein, the term "distal" refers to a downstream position in vessel 152, while the term "distally" refers to downstream movement in a distal direction 140.

Additionally, as used herein, the term proximal refers to an upstream position in vessel 152, while the term proximally refers to an upstream movement in a proximal direction 142.

MB guidewire 156 has been fed distally in direction 140 to pass through MB proximal vessel segment 120 and an MB distal vessel segment 122. SB guidewire 146 has been fed distally in direction 140 to pass through MB distal vessel segment 120 and SB vessel segment 124.

With MB guidewire 156 and SB guidewire 146 in place, as seen in FIG. 3, bifurcated balloon 100 is loaded on MB guidewire 156 and SB guidewire 146 so that SB guidewire 146 passes through SB guidewire lumen 116 and MB guidewire 156 passes through MB guidewire lumen 136.

Bifurcated balloon 100 is then advanced in distal direction 140 through MB vessel proximal segment 120 toward MB distal vessel segment 122 and SB vessel segment 124, herein a targeted bifurcation 138.

Longitudinal SB extension tube 112 has a smaller cross-sectional area than SB proximal balloon portion 134, aiding in ease of advancement, and positioning SB proximal balloon portion 134 in spite of narrowing that may be present in MB proximal vessel branch 120 prior to reaching targeted bifurcation 138.

FIG. 4 shows bifurcated balloon 100 in an unexpanded configuration, within targeted bifurcation 138.

FIG. 5 shows preparation of bifurcated balloon 100 for inflation. In deployment of bifurcated balloon, there are two options, either of which may be used by the operator. The most common scenario as seen in some embodiments, SB guidewire 146 is left in place until bifurcated balloon 100 has been inflated and deflated. Then the bifurcating balloon is withdrawn over wires both wire 146 and wire 156 which are maintained in segments 124 and 122 respectively.

Alternatively, wire 146 is removed at any stage prior to withdrawing balloon 100 and balloon 100 is withdrawn over wire 156.

FIG. 6 shows stenotic tissue 126 being displaced outwardly in response to the inflation of bifurcated balloon 100. Bifurcated balloon 100 can be inflated and deflated several times to ensure that stenotic tissue 126 assumes a substantially fixed radial outward position with respect to bifurcated vessel 152.

At the conclusion of the intervention, bifurcated balloon 100 is withdrawn proximally, in direction 142, over guidewire 146 and guidewire 156; or (as noted above) over guidewire 156 alone. After vessel imaging demonstrates satisfactory results guidewire 146 and/or 156 are withdrawn proximally in direction 142.

FIG. 7 shows bifurcated stent balloon 190 adapted for transporting a stent 150 to targeted bifurcation 138.

Bifurcated stent 150 includes a proximal MB stent portion 160 aligned with proximal MB balloon portion 130, a distal MB stent 162 aligned with distal MB balloon portion 132 and an SB stent 164 aligned with side branch (SB) balloon portion 134.

Bifurcated stent balloon 190 and stent 150 are introduced through MB proximal vessel segment 120 in the unexpanded configuration, similar to that shown in FIGS. 3 through 5.

Prior to inflation of bifurcated balloon 190, SB guidewire 146 is removed in proximal direction 142 and bifurcated balloon 190 has been inflated, thereby expanding stent 150 radially outward to compress and to clear vessel 152 of stenotic tissue 126.

Bifurcated stent balloon 190 typically minimally protrudes (overhangs) beyond the edges of stent 150.

FIG. 8 shows stent 150 in an expanded configuration at targeted bifurcation 138 while bifurcated stent balloon 190 and MB guidewire 156 are withdrawn in proximal direction 142 out of MB vessel 120 at the end of the procedure.

Figure 9:
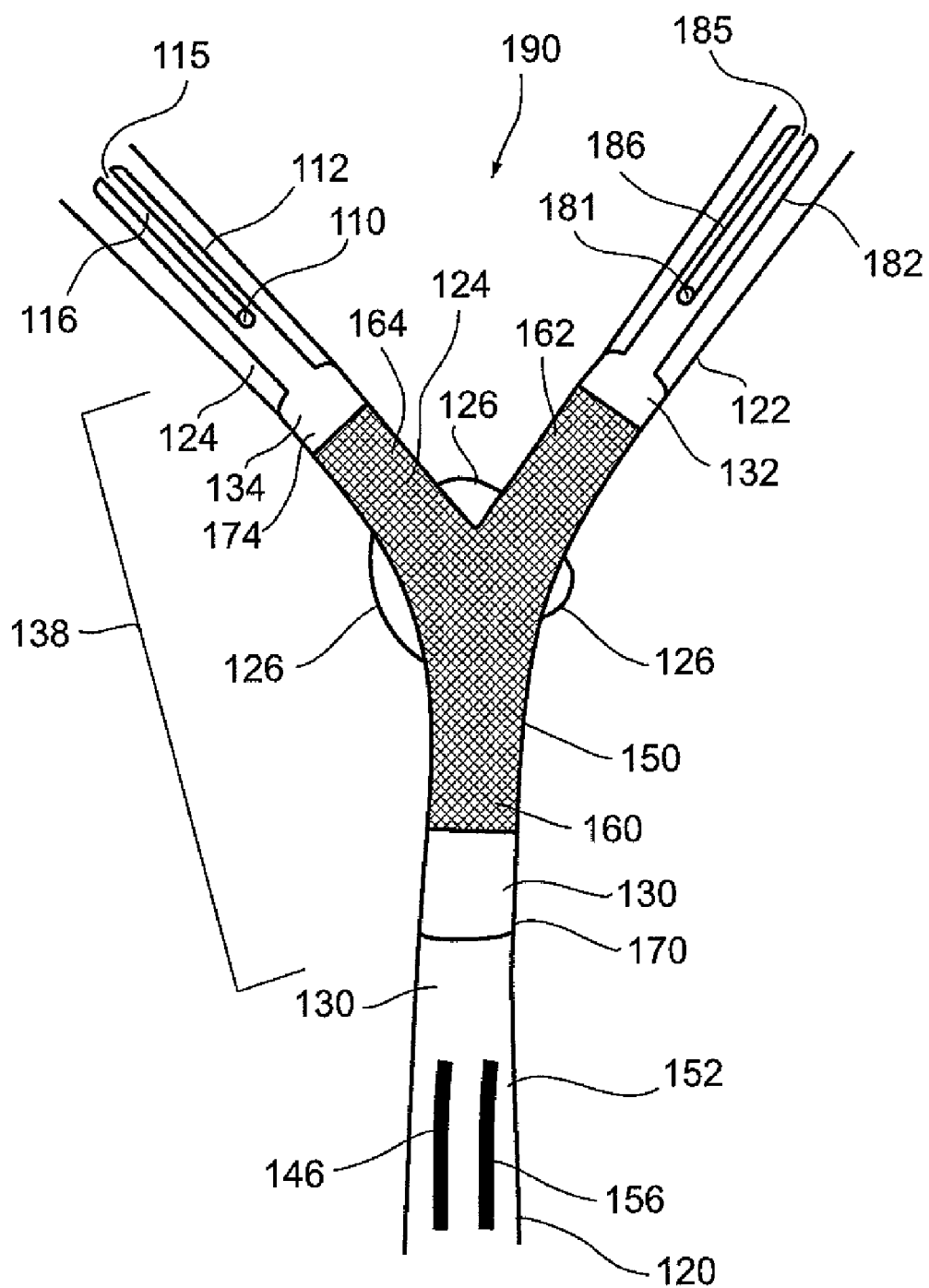

FIG. 9 shows a bifurcating balloon 190 configured with a distal MB extension tube 182 having a guidewire lumen 186 that includes a proximal opening 181 and a distal opening 185 through which guidewire 156 is fed prior to deployment of stent 150.

Similar to SB extension tube 112 noted above, distal MB extension tube 182 has a smaller cross-sectional area than MB distal balloon portion 132 to aid in placement of stent 150. Distal MB extension tube 182 in addition to SB extension tube 112 has potentially simplifies manufacture and design of bifurcating balloon 190.

Additionally, distal MB extension tube 182 reduces the profile of bifurcating balloon 190, rendering this application desirable where proximal segment 120 and/or distal MB vessel branch segment 122 are significantly constricted.

There is further provided a method of providing a bifurcated self-expanding stent and advancing and positioning the bifurcated self-expandable stent using either one or two longitudinal tubular extension tubes which may be positioned distal to the stent and which accommodate the guide wire on which the self expandable stent is advanced.

The materials and dimensions that follow reference both FIGS. 1 and 7: In embodiments, bifurcated balloon 100 and bifurcated stent balloon 190 have a minimal inflation diameter of at least about 2.0 millimeter. In embodiments, bifurcated balloon 100 and bifurcated stent balloon 190 have a maximum inflation diameter of no more than about 40 millimeters applicable to all coronary and peripheral interventions at any vascular location.

In embodiments, bifurcated balloon 100 and bifurcated stent balloon 190 have a wall thickness of at least about 0.01 millimeters. In embodiments, bifurcated balloon 100 and bifurcated stent balloon 190 have a wall thickness of no more than about 0.5 millimeters. However, thickness of material will depend on technology and minimal traits and characteristics as require by current industry standards for a given targeted bifurcation 138.

In embodiments of the present invention, distal MB balloon portion 132 and SB balloon portion 134 are optionally of substantially different dimensions, including length, expanded diameter, and/or unexpanded diameter.

In other embodiments of the present invention distal MB balloon portion 132 and proximal MB balloon portion 130 are optionally substantially of different dimensions, including length, expanded diameter and/or unexpanded diameter.

In further embodiments of the present invention distal SB balloon portion 134 and proximal MB balloon portion 130 are optionally substantially of different dimensions, including length, expanded diameter and/or unexpanded diameter.

In embodiments, bifurcated balloon 100 and bifurcated stent balloon 190 have an unexpanded and expanded length between 12-150 mm, depending on the dimensions of targeted bifurcation 138.

In embodiments, bifurcated balloon 100 and bifurcated stent balloon 190 have an expanded diameter of 2-50 mm depending on the dimensions of targeted bifurcation 138.

In embodiments, bifurcated balloon 100 and bifurcated stent balloon 190 have a pre-deployed diameter of 0.2-8 mm, depending on the dimensions of targeted bifurcation 138.

In embodiments inflated and deployed bifurcated balloon 100, bifurcated stent balloon 190 and stent 150 have an angle between their bifurcated portions ranging from 0-180 degrees depending on the angulation of targeted bifurcation 138.

In embodiments, bifurcated balloon 100, bifurcated stent balloon 190 and stent 150 have an angle between their bifurcated portions of an angle of less than about 30°, in their pre-inflated and pre-deployed configuration.

In embodiments, bifurcated balloon 100 and bifurcated stent balloon 190 comprise a material selected from the group consisting of: synthetic biostable polymer, a natural polymer, and an inorganic material. In embodiments, the biostable polymer comprises a material from the group consisting of: a polyethylene, a polyolefin, a polyurethane, a fluorinated polyolefin, a chlorinated polyolefin, a polyamide, an acrylate polymer, an acrylamide polymer, a vinyl polymer, a polyacetal, a polycarbonate, a polyether, an aromatic polyester, a polyether (ether keto), a polysulfone, a silicone rubber, a thermoset, and a polyester (ester imide).

In embodiments, the natural polymer comprises a material from the group consisting of a polyolefin, a polyurethane, a Mylar, a silicone, a polyester and a fluorinated polyolefin.

Although described with respect to treating bifurcated vessels of the cardiovascular system, and especially bifurcated arteries, the teachings of the present invention are generally applicable to many different cardiovascular and non-cardiovascular applications. Specific cardiovascular applications include, but not limited to, the deployment of bifurcated balloon 100, bifurcated stent balloon 190, bifurcated self expandable stent and bifurcated stent 150 in atherosclerotic, or other occlusive arterial and/or venous vascular disease, ectatic arteries and ectatic arteries containing an obstructive lesion, aneurismatic arteries, saphenous vein grafts and native arteries, coronary or any arterial perforation, coronary arterial fistula, aortic abdominal aneurysm and other aneurismatic peripheral arteries, transjugular intrahepatic portal shunt, percutaneous transluminal angioplasty, fistula closing and neuro interventions (such as aneurysms and arterial-venous malformations), small vessel intraluminal grafting, and ostial renal artery lesions.

With respect to the teachings of the present inventions, cardiovascular vessels include, inter alia, coronary arteries, carotid arteries, renal arteries, iliofemoral popliteal and infrapopliteal arteries, aorta and aortic arch arteries, and mesenteric arteries.

Additional non-cardiovascular applications include, intra alia, urological, gastroenterological, respiratory, venous and neurological applications.

It is expected that during the life of this patent many relevant bifurcated balloon designs and materials will be developed and the scope of the term bifurcated balloon is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A bifurcated balloon for in vivo use, comprising:
   i) a proximal hollow tubular element;
   ii) two bifurcating hollow tubular elements extending distally from a distal end of said proximal hollow tubular element, said two elements comprising:
      a) a first distal tubular element guidable into a first distal main branch of a vessel bifurcation; and
      b) a second distal tubular element having a proximal end and a distal end and being guidable into a second, side, branch of said vessel bifurcation;
   iii) a longitudinal central chamber extending from a distal end of said first distal tubular element into said proximal hollow tubular element, said second distal tubular element having an extension member extending from the distal end of said second distal tubular element, said extension member comprising a first guidewire channel, said first guidewire channel comprising a distal tip and a proximal tip and a distal end opening at said distal tip and a side opening at said proximal tip, said side opening at said proximal tip being adjacent to a distal end of said second distal tubular element; and iv) a second substantially longitudinal guidewire channel passing through said proximal hollow tubular element and said first distal tubular element, said second guidewire channel having two ends of which a first end passes through a proximal portion of said longitudinal chamber, and said second end of said second substantially longitudinal guidewire channel passes through said first distal tubular element, said second guidewire channel having an opening at a distal end of said first distal tubular element and a further opening at a proximal end of said proximal tubular element.

2. The apparatus of claim 1, including a first guidewire insertable through said first guidewire channel.

3. The apparatus of claim 1, including a second guidewire insertable through said second substantially longitudinal guidewire channel.

4. The apparatus of claim 1, including a catheter channel from a proximal end of said proximal hollow tubular element.

5. A method of manufacturing a rapid exchange bifurcated balloon, comprising:
   a) extending a first longitudinal distal tubular extension from a distal end of a first of two distal balloon portions extending from a proximal portion of a bifurcated balloon;
   b) providing a longitudinal central chamber to extend from a distal end of a second distal balloon portion into said proximal portion of said bifurcated balloon into a catheter shaft, said first distal balloon portion being devoid of a longitudinal central chamber; and
   c) creating a first guidewire channel through said tubular extension with a proximal side opening distal to said distal end of said first distal balloon portion and a second guidewire channel extending through said longitudinal central chamber.

6. A method of deploying a bifurcated balloon, comprising:
   a) providing a bifurcated balloon having a first guidewire channel through a proximal balloon portion and a first distal balloon portion, the first guidewire channel passing through a longitudinal central chamber extending from a distal end of said first distal balloon portion into said proximal balloon portion, said second distal balloon portion having an extension member extending from the distal end of said second distal tubular element, said extension member comprising a second guidewire channel, said second guidewire channel comprising a distal tip and a proximal tip and a distal end opening at said distal tip and a side opening at said proximal tip, said side opening at said proximal tip being adjacent to a distal end of said second distal balloon portion;
   b) passing a first guidewire through a proximal main branch (MB) vessel and a distal MB vessel and a second guidewire through said proximal MB vessel and a side branch (SB) vessel;
   c) feeding said first guidewire channel over said first guidewire;
   d) feeding said second guidewire channel over said second guidewire;
   e) moving said bifurcated balloon upward along said first and second guide wires; and
   f) visualizing said proximal and said first distal portion of said bifurcated balloon portion in said MB vessel and said second distal portion of said bifurcated balloon in said SB vessel.

7. The method of claim 6 including:
   g) inflating said bifurcated balloon;
   h) deflating said bifurcated balloon; and
   i) removing said bifurcated balloon from said SB vessel and said MB vessel.

* * * * *